United States Patent
Ikhlef et al.

(10) Patent No.: US 10,473,796 B2
(45) Date of Patent: Nov. 12, 2019

(54) SCINTILLATING ARRAY WITH ALIGNMENT FEATURES

(71) Applicant: FMI Medical Systems Co., Ltd., Zhejiang (CN)

(72) Inventors: Abdelaziz Ikhlef, Hudson, OH (US); Kevin McMahon, Mentor, OH (US); Mark McElroy, Akron, OH (US)

(73) Assignee: FMI Medical Systems Co., Ltd., Zhejiang (CN)

(*) Notice: Subject to any disclaimer, the term of this patent is extended or adjusted under 35 U.S.C. 154(b) by 134 days.

(21) Appl. No.: 15/890,653

(22) Filed: Feb. 7, 2018

(65) Prior Publication Data
US 2019/0243006 A1    Aug. 8, 2019

(51) Int. Cl.
| | |
|---|---|
| *G01T 1/20* | (2006.01) |
| *A61B 6/03* | (2006.01) |
| *A61B 6/00* | (2006.01) |
| *G01T 1/29* | (2006.01) |
| *G01T 7/00* | (2006.01) |

(52) U.S. Cl.
CPC .............. *G01T 1/20* (2013.01); *A61B 6/4291* (2013.01); *A61B 6/5282* (2013.01); *G01T 1/2985* (2013.01); *A61B 6/032* (2013.01); *A61B 6/5205* (2013.01); *G01T 7/005* (2013.01)

(58) Field of Classification Search
CPC ..... A61B 6/032; A61B 6/4291; A61B 6/5205; A61B 6/5282; G01T 1/20; G01T 1/2985; G01T 7/005
See application file for complete search history.

(56) References Cited

U.S. PATENT DOCUMENTS

| | | | |
|---|---|---|---|
| 5,991,357 A * | 11/1999 | Marcovici | A61B 6/035 250/370.09 |
| 7,233,640 B2 | 6/2007 | Ikhlef et al. | |
| 2006/0289765 A1 | 12/2006 | Ikhlef et al. | |
| 2013/0108019 A1 | 5/2013 | Tkaczyk et al. | |

* cited by examiner

*Primary Examiner* — Mark R Gaworecki
(74) *Attorney, Agent, or Firm* — Fishman Stewart PLLC

(57) ABSTRACT

A scintillator module for a CT detector includes an array of pixelated scintillators extending in a first direction at a first spacing, and extending in a second direction at a second spacing, a reflector on the array and between the pixelated scintillators, the reflector having a first thickness and forming notches having a second thickness that is greater than the first thickness. The module includes an anti-scatter grid having plates, each plate extending along a length such that, when the CT detector is positioned in a CT system, the length of the plates extend approximately toward a focal spot. The plates are separated from one another at one of the first spacing and the second spacing, and two of the notches have a gap therebetween that engages one of the plates. An adhesive positioned in the gap to adhere the one plate to the reflector.

20 Claims, 7 Drawing Sheets

SCINTILLATING ARRAY WITH ALIGNMENT FEATURES

TECHNICAL FIELD

This disclosure relates generally to diagnostic imaging and, more particularly, to an apparatus and method of fabricating a detector for a Computed Tomography (CT) system.

BACKGROUND

Typically, in CT imaging systems, a rotatable gantry includes an x-ray tube, detector, data acquisition system (DAS), and other components that rotate about a patient that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into photons within the scintillator, and then to electrical signals within the photodiode. The electrical signals are digitized and then received within the DAS, processed, and the processed signals are transmitted via a slipring (from the rotational side to the stationary side) to a computer or data processor for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Imaging data may be obtained using x-rays that are generated at a single average energy, corrected from a polychromatic energy spectrum. However, some systems may obtain multi-energy images that provide additional information for generating images.

Third generation multi-slices CT scanners are built with detectors that include scintillator/photodiodes arrays. These detectors are positioned in an arc where the focal spot is the center of a corresponding circle. The material used in these detectors generally use scintillation crystal/photodiode arrays, where the scintillation crystal absorbs X rays and converts the absorbed energy into visible light. A photodiode is used to convert the light to an electric current.

In recent years the development of volumetric (VCT) or cone-beam CT (CBCT) technology has led to a rapid increase in the number of slices used in CT detectors. The detector technology used in large coverage CT enables greater and greater coverage in patient scanning by increasing area exposed. In CT detectors, the increase of the number of slices results in an increase in the width of the detector along a length of the patient, or commonly referred to as the Z-axis.

The x-ray detectors of current state of the art CT systems include a two-dimensional (2D) array of scintillating pixels, coupled to a 2D array of Si photodiodes. A typical detector can include an array of 16, 32, 64, or more. However, recently the need for cardiac imaging has gotten more interest, with the goal of imaging the heart within one rotation. In order to image the heart in one rotation, for common gantries the detector size is therefore approximately 140 mm to 160 mm (at iso-center or "ISO") to cover the full organ in half scan (which in one example is equivalent to a detector having approximately 256 slices).

Building very large modules in a monolithic structure to cover 160 mm in z-axis coverage includes numerous challenges, such as manufacturing cost and reliability. To reduce cost, one known method includes abutting smaller modules to have more than one module extending along the Z-axis. In such a design, each module may include its own collimator attached to the surface of the scintillator, and as indicated one or more modules may thereby be built into a larger structure, extending in a Z-direction.

However, alignment of collimators with their respective scintillator can be challenging, and may include optical alignment features to position the collimator with respect to pixels of the scintillator. Optical placement can be difficult, in that alignment of the relatively deep (in a Y-direction) of the collimator may not be possible due to the depth of the scintillator, and individual pixels of the scintillator themselves may not be visible during assembly.

In addition, adhesion to the scintillator can also be a challenge, as the scintillator is typically covered with reflector material to prevent stray light from passing to the pixels, and the reflector on the scintillator may not have sufficient surface adhesion characteristics to obtain or maintain robust and reliable adherence during the life of the detector.

Thus, there is a need to improve the scintillator adhesion to the collimator, precise alignment and assembly thereof.

BRIEF DESCRIPTION

A scintillator module for a CT detector includes a grid of pixelated scintillators extending in a first direction at a first spacing, and extending in a second direction, orthogonal to the first direction, at a second spacing, a reflector on the grid and between the pixelated scintillators, the reflector having a first thickness, the reflector forming a plurality of notches having a second thickness that is greater than the first thickness, an anti-scatter grid having a plurality of plates, each plate extending along a length such that, when the CT detector is positioned in a CT system, the length of the plates extend approximately toward a focal spot of the CT system, the plurality of plates separated from one another at one of the first spacing and the second spacing, wherein two of the notches have a gap therebetween that engages one of the plates, and an adhesive positioned in the gap to adhere the one plate to the reflector.

A method of fabricating a scintillator module for a CT detector includes forming a grid of pixelated scintillators extending in a first direction at a first spacing, and extending in a second direction, orthogonal to the first direction, at a second spacing, adhering a reflector to the grid and between the pixelated scintillators, the reflector having a first thickness, forming a plurality of notches with the reflector, the notches having a second thickness that is greater than the first thickness, positioning an anti-scatter grid on the reflector, the anti-scatter grid having a plurality of plates, each plate extending along a length such that, when the CT detector is positioned in a CT system, the length of the plates extend approximately toward a focal spot of the CT system, the plurality of plates separated from one another at one of the first spacing and the second spacing, wherein two of the notches have a gap therebetween that engages one of the plates, and applying an adhesive to the gap to adhere the one plate to the reflector.

A CT system includes a rotatable gantry having an opening for receiving an object to be scanned, an x-ray tube having a focal spot from which x-rays emit, and a detector comprising one or more scintillator modules for receiving x-rays from the focal spot. Each of the one or more scintillator modules includes a grid of pixelated scintillators extending in a first direction at a first spacing, and extending in a second direction, orthogonal to the first direction, at a second spacing, a reflector on the grid and between the pixelated scintillators, the reflector having a first thickness, the reflector forming a plurality of notches having a second thickness that is greater than the first thickness, an anti-scatter grid having a plurality of plates, each plate extending along a length such that the length of the plates extend approximately toward the focal spot, the plurality of plates separated from one another at one of the first spacing and the second spacing, wherein two of the notches have a gap therebetween that engages one of the plates, and an adhesive positioned in the gap to adhere the one plate to the reflector. The system includes a computer programmed to acquire imaging data and generate an image.

Various other features and advantages will be made apparent from the following detailed description and the drawings.

DETAILED DESCRIPTION

The operating environment of disclosed embodiments is described with respect to a multislice computed tomography (CT) system. Embodiments are described with respect to a "third generation" CT scanner, however it is contemplated that the disclosed embodiments are applicable to other imaging systems as well.

Figure 1:
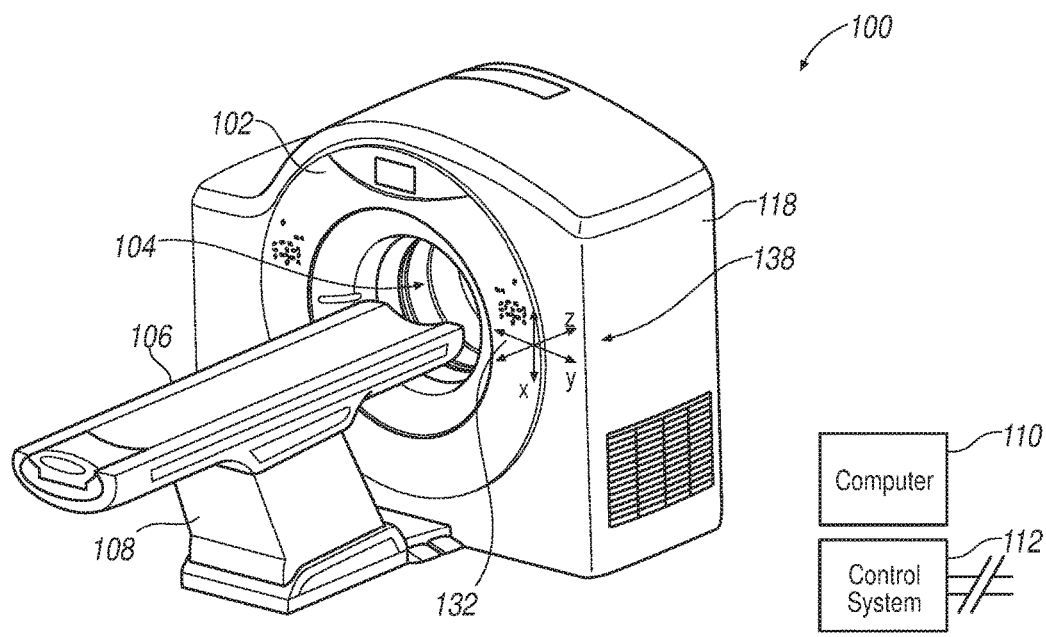
FIG. 1 is a perspective view of a CT imaging system.
Figure 2:
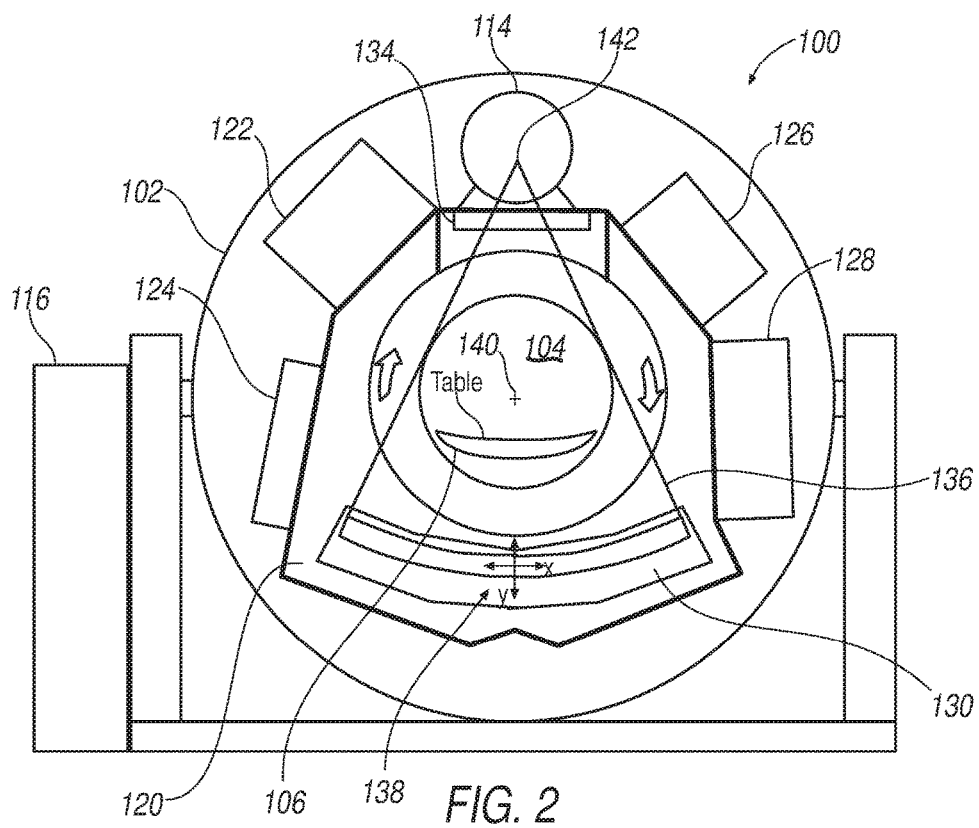
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction algorithms, or an image reconstructor may be provided as a separate processing unit. Control system 112 provides control commands for operating gantry 102, an x-ray tube 114, a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is caused to rotate about the patient up to typically a few Hz in rotational speed, and table 106 is caused to move the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals are digitized and passed to DAS 124, and then to computer 110 where the data is further processed to generate an image. The imaging data may be stored on computer system 100 and images may be viewed. An X-Y-Z triad 138, corresponding to a local reference frame for components that rotate on rotatable base 120, defines a local directional coordinate systems in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
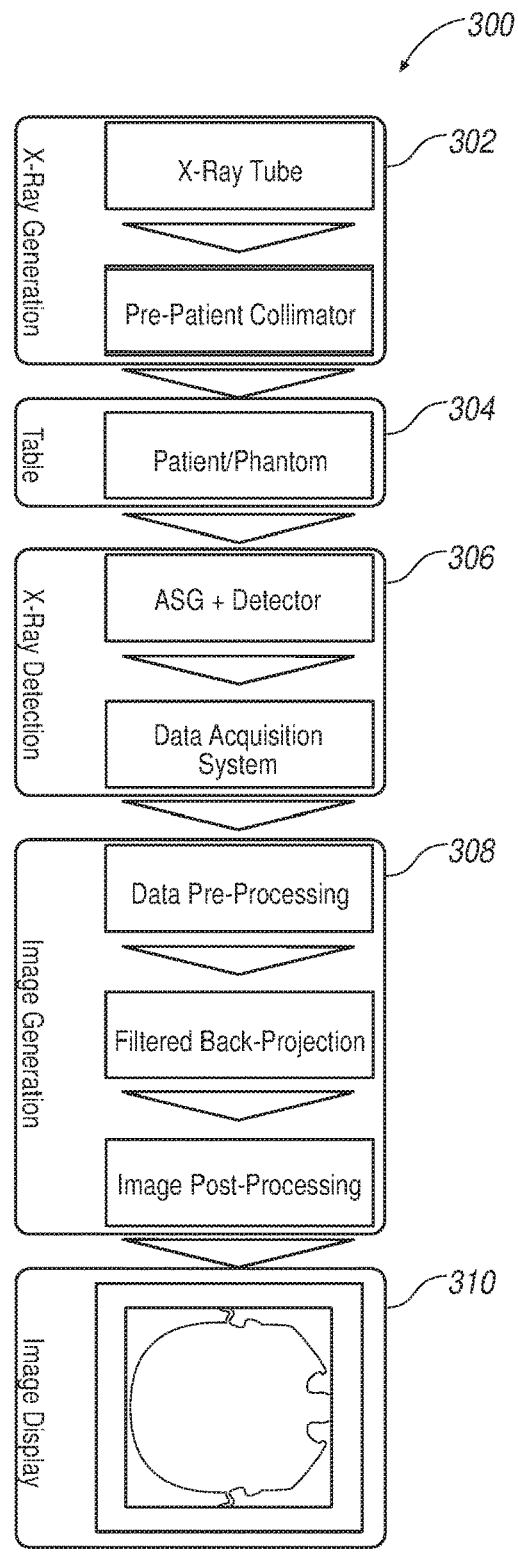
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which time table 106 passes 304 through opening 104 of gantry 102. In one example table 106 may have a patient thereon, and in another example a phantom may be used for calibration purposes.

X-ray detection 306 occurs when x-rays having emitted from x-ray tube 114 pass to detector assembly 130. An anti-scatter grid (ASG) prevents x-ray scatter (emitting for example from the patient as secondary x-rays and in a direction that is oblique to x-ray beam 136), by generally passing x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
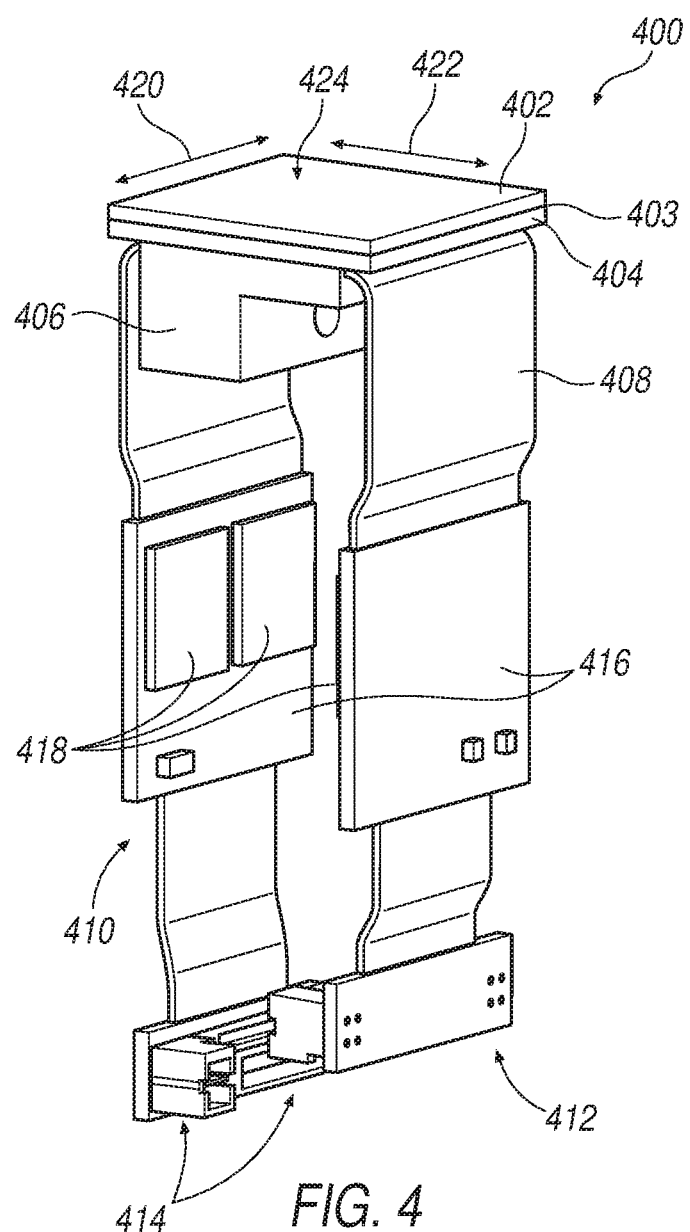
FIG. 4 illustrates a module or mini-module not yet having a collimator attached.

FIG. 4 illustrates a module or mini-module 400 having been assembled according to the disclosure, not yet having a collimator (ASG) attached thereto. Module 400 includes a grid of pixelated scintillators or scintillating array 402 positioned on a substrate 404, having a photodiode 403 therebetween. An alignment block 406 mechanically supports module 400. Positioned between alignment block 406 and substrate 404 is a flex circuit 408, which wraps within module 400 and includes a first end 410 and a second end 412. Each end 410, 412 includes electrical connectors 414, a circuit board or electronics package 416, ASIC or processors 418, and other associated electronic components (not shown). Module 400, when placed on a gantry of a CT system, such as system 100 above, has an orientation of a Z or slice direction 420 and an X or channel direction 422. Grid or scintillating array 402 includes an upper surface 424, having features described with respect to FIG. 5.

Figure 5:
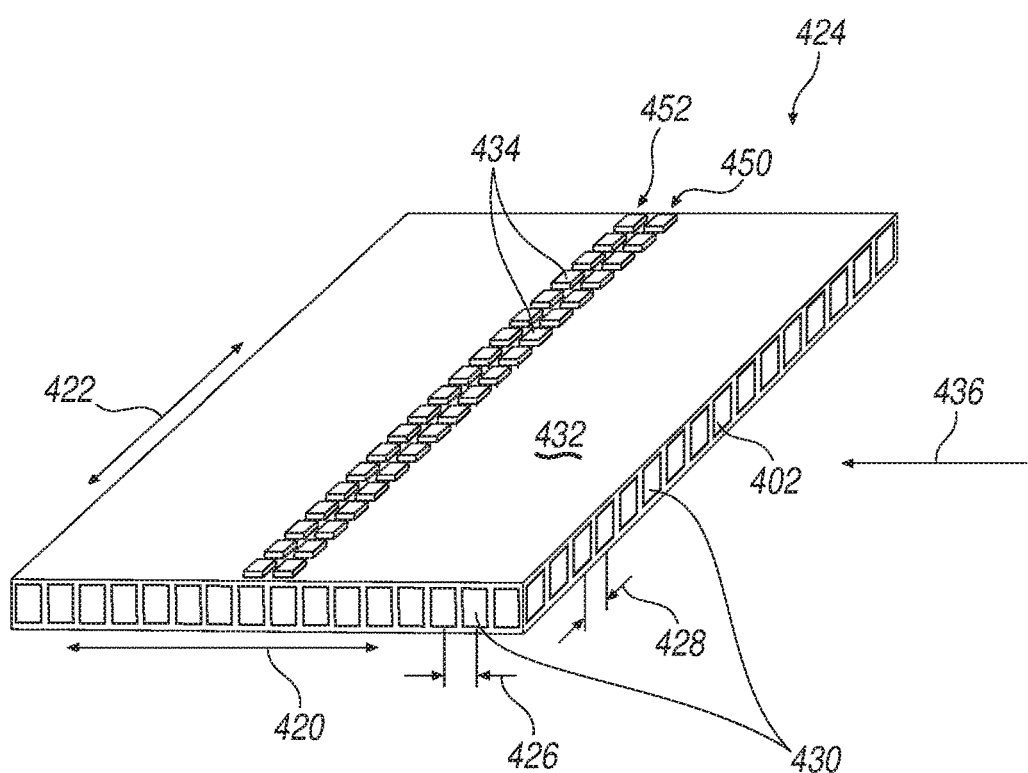
FIG. 5 illustrates a scintillating array having a reflector and notches.

Referring to FIG. 5, scintillating array 402 having upper surface 424 is shown, and having pixels extending in the Z or slice direction 420 at a spacing 426, and extending in the X or channel direction 422 (orthogonal to the Z or slice direction 420) at a spacing 428. In one example spacing 426 may be equal to spacing 428 and in which each pixel 430 may be approximately square, and spaced apart from one another an equal amount in both directions 420, 422. In another example, pixels 430 may have rectangular shapes, in which case spacing 426 and 428 are not equal, and in which pixels 430 may be spaced apart from one another unequal amounts in both directions 420, 422.

Array 402 includes a reflector layer or coating 432 on an upper surface of each of pixels 430, as well as between pixels 430. Reflector 432 is formed of a material such as an epoxy that may include optically absorbent material, to absorb light that may otherwise transmit as cross-talk between pixels 430. That is, reflector 432 itself may reflect light as it passes within pixels 430. Thus, other optically absorbent material may be incorporated within reflector 432 to optimize or strike a balance between the amount of reflection in a pixel and the amount of cross-talk therein. Reflector 432 includes a plurality of notches 434, as will be further described.

Figure 6:
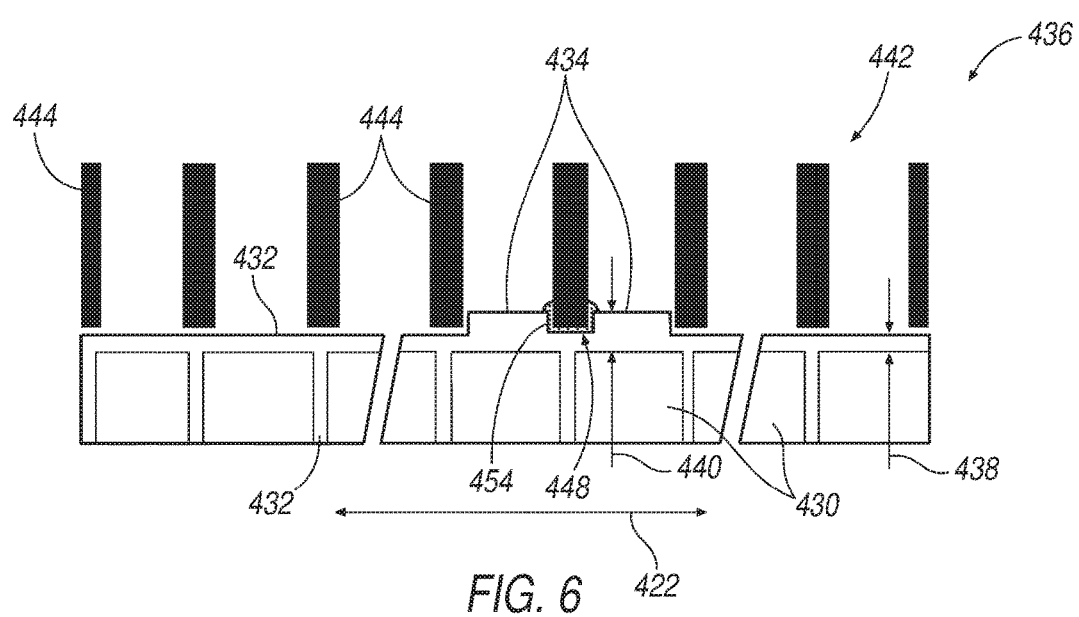
FIG. 6 illustrates a side view of pixels corresponding with FIG. 5.

Referring to FIG. 6, a view 436 of pixels 430 corresponds with direction 436 as shown in FIG. 5. View 436 shows reflector 432 on top of and between pixels 430. Reflector 432 positioned on top of pixels 430 includes a thickness 438 of reflector material. Thickness 438 may have a desired thickness of 100-300 µm, and in one example, thickness 438 is 200 µm. It is contemplated, however, that thickness 438 may be any thickness such that adequate reflection and absorption of light occurs and so that image quality is not compromised. As such, thickness 438 is selected based at least in part on the types of materials used, as well as any optically absorbent material that may be included, as well.

Figure 7:
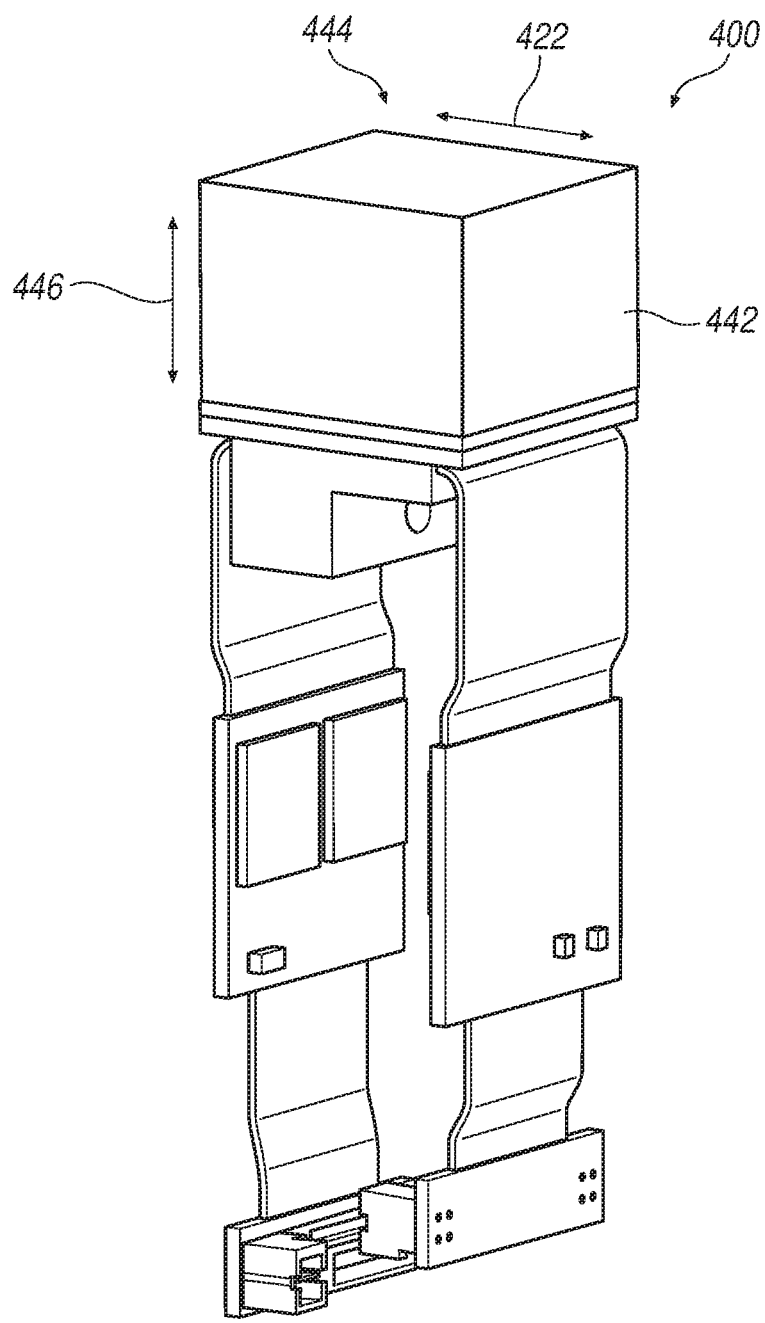
FIG. 7 illustrates the module or mini-module of FIG. 4 having a collimator attached.

Reflector 432 therefore has a first thickness 438, but includes notches 434 formed of reflector material. That is, the reflector forms a plurality of notches 434 having a second thickness 440 that is greater than first thickness 438. An anti-scatter grid 442 having a plurality of plates 444 is positioned on upper surface 424 of scintillating array 402. Referring to FIG. 7, module 400 of FIG. 4 is shown including anti-scatter grid 442 positioned thereon.

In the example shown, anti-scatter grid 442 is a monolithic device having plates that extend in X or channel direction 422. Anti-scatter grid 442 in the illustrated example may be fabricated using a plurality of tungsten plates, or as another example may be fabricated using 3D printing technology and having high density materials such as tungsten or other x-ray absorbing materials therein. Accordingly, in one example, anti-scatter grid 442 is a two-dimensional (2D) collimator with plates 444 spaced from one another having a spacing that corresponds with a spacing of each of pixels 430. Referring to FIG. 6, such spacing may correspond with X or channel direction 422.

Plates 444 may thereby be fabricated in anti-scatter grid 442 to be slightly non-parallel to one another so that each may be directed and approximately aimed toward a focal spot of a CT system. For instance, referring back to FIG. 2, modules 400 may be positioned accordingly within CT detector assembly 130 and on gantry 102, having each plate 444 extending along a length and in a direction 446 such that, when CT detector 130 is positioned in CT system 100, the length of plates 444 extend 446 approximately toward focal spot 142 of CT system 100.

According to the disclosure, in one example notches 434 have a gap or spacing 448 therebetween, such that anti-scatter grid 442 may be mechanically aligned and positioned therewith. That is, being a monolithic piece, anti-scatter grid 442 may be mechanically and precisely located having one of plates 444 positioned within gap 448. As such, anti-scatter grid 442 may be placed extremely accurately, within typically a few µm of desired location, by having both anti-scatter grid 442 and notches 434 being fabricated with high tolerance control. That is, because each anti-scatter grid 442 is fabricated having a high and tight tolerance, and likewise notches 434 may be fabricated having high and tight tolerances, then the placement of anti-scatter grid 442 with respect to pixels 430 may likewise be tightly controlled. Further, tolerances are controlled at a local level and global tolerances may not build up in the construction of a large monostructure such as CT detector 130.

In the above example, anti-scatter grid 442 is a 2D grid of plates 444. Thus, it may not be necessary to place plates 444 along Z or slice direction 420 to such as degree of high tolerance, given that the exemplary 2D collimator does not collimate, in this example, in the Z or slice direction 420. However, in one example anti-scatter grid 442 may be a three-dimensional (3D) grid, having plates extending in both channel and slice directions 422, 420. As such, placement in both directions 420, 422 may be controlled by including appropriate dimensional placement and sizing of notches 434. That is, dimensional tolerances for both placement and size of notches 434 may be appropriately controlled so that placement of anti-scatter grid 442 as a 3D grid may be controlled equally well in both directions.

In one example, notches 434 may be placed offset from one another along Z or slice direction 420. Referring back to FIG. 5, notches 434 include a first row 450 and a second row 452. Notches 434 in each row 450, 452 may thereby include an increased surface area for adhesion of anti-scatter grid 442 to surface 424, compared to a single row. And, although two rows 450, 452 are shown, it is contemplated three, four, or even more rows of notches may be included, according to the disclosure, to provide an increased amount of surface area for adhesion purposes.

Accordingly, referring again to FIG. 6, a glue or adhesion bead 454 may be included in gap 448 to adhere plate 444 between notches 434, and thereby anti-scatter grid 442 in whole to surface 424. Glue or adhesion bead 454 may include an epoxy or other material that provides sufficient adhesion strength for the life of the detector, with any anticipated radiation damage that the adhesive of bead 454 may experience. In such fashion, a 2D grid may be placed accurately and in the fashion shown in FIG. 6. And, in one example, gap 448 may have a width that is approximately the same thickness as a thickness as one of plates 444. Further, and as illustrated, each of plates 444 is positioned to cover a respective gap between the pixelated scintillators 430.

Figure 8:
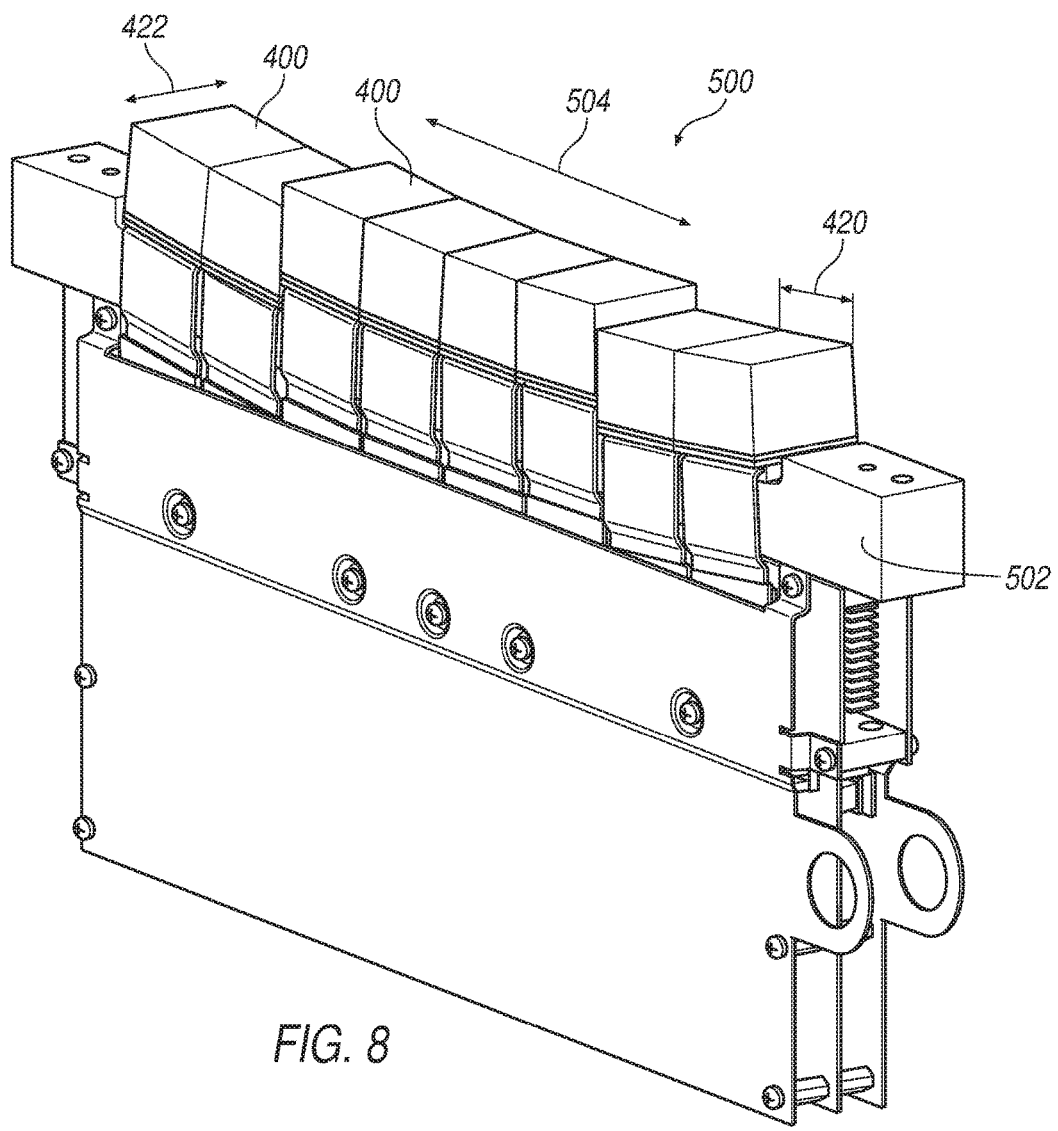
FIG. 8 a detector sub-assembly having a plurality of modules.

Referring now to FIG. 8, a detector sub-assembly 500 shows a plurality of modules 400, being positioned on an alignment block 502. As shown, each module 400 includes Z or slice direction 420, which combine to provide a composite coverage in a system Z direction 504, which corresponds with triad 138 in FIGS. 1 and 2. Correspondingly, each module 400 includes X or channel direction 422, and modules 400 are thereby combined or stacked side-by-side to form a plurality of detectors, corresponding with triad 138 of FIGS. 1 and 2, forming detector assembly 130. Thus, according to the disclosure, each module 400 is fabricated in the fashion described herein, having notches 434 that form a local reference feature for each module 400, locating each anti-scatter grid 442. As such, global system tolerances do not accumulate, such as if all plates 444 were placed with respect to alignment block 502, for example. In addition, each module 400 may be classified and placed within the detector according to the measured quality of the modules.

Accordingly, the disclosed architecture includes an accurate process in stacking and classification of mini-modules, with a precise mechanical packaging which enables precise alignment, removability and repairability.

In this disclosure, in one example the mini-module elements include 32×32 arrays, with 8 mini-modules along system Z direction 504, to achieve 256 by stacking them in a curved Z-axis as shown. It is contemplated that more or less overall slices may be achieved, as well, by stacking the number of modules in Z, accordingly.

In the disclosed design both X-axis and Z-axis are curved to form a sphere where focal spot 142 is the center of the sphere. Using a spherical structure is motivated to use a 2D anti scatter grid of the 32×32 array. Thus, the disclosure uses mini-modules and stacks them on a curved frame or structure along the Z-axis, to form a sphere.

FIG. 7 illustrates a basic unit of the detector called, in one example, a mini-module. In this example, the mini-module includes a 32×32 pixel crystal array on photodiode, and the equipment used to digitize the signal. To complete the mini-module, an anti-scatter grid (ASG) is glued to the array surface and an alignment and mounting block to the back of the photodiode substrate. However, to attach the 2D ASG, protrusions or notches are added on the top reflector, forming grooves which will receive the ends of the 2D anti-scatter grid, allowing them to be aligned during the attachment and curing process. FIG. 5 shows the protrusion or notch features on the top reflector of the scintillating array.

Benefits that accrue, based on the disclosure, include a capability of modules to achieve different sizes of detector coverage without redesign (such as 32 slice, 64 slice, 128 slice, or 256 slice, as examples). Alignment of each anti-scatter grid to the scintillation array is simplified and more accurate, as compared to devices typically fabricated in a global fashion (i.e., having plates aligned with respect to a single base structure, such as alignment block 502). Use of min-modules thereby enables a spherical detector structure, also using an anti-scatter grid element. Having improved placement of the anti-scatter grid to the scintillator minimizes sensitivity to thermal drift because of accurate alignment to kerfs or cut edges of the scintillation array. Because of the improved placement of the anti-scatter grid relative to the scintillator, tighter tolerances may thereby be achieved, reducing a gap size between modules and by appropriately adjusting the detector arc radius for the modules. The modules themselves may be not only more accurately placed, compared to a collimator having a global reference frame, but they may be easily removed and replaced as may necessary during both fabrication and repair of the detector.

Further, each module may be separately tested and repaired, simplifying overall detector construction and manufacturability. That is, in the event of component failure in, for instance one of the circuit boards, then repair of the detector only entails repair of one module itself, as opposed to repair of perhaps the entire detector. Each module may also be tested as a single device before installation into the detector. Image quality may be improved as well, in that placement of the anti-scatter grid is very precise, typically within a few µm, compared to the scintillator array.

Having single modules that are placed into sub-assemblies (such as 8, as shown in FIG. 8), the size of the detector becomes scale-able at will, adding more modules as may be desired.

Disclosed also is a method of fabricating a scintillator module for a CT detector. The method includes forming a grid of pixelated scintillators extending in a first direction at a first spacing, and extending in a second direction, orthogonal to the first direction, at a second spacing, adhering a reflector to the grid and between the pixelated scintillators, the reflector having a first thickness, forming a plurality of notches with the reflector, the notches having a second thickness that is greater than the first thickness, positioning an anti-scatter grid on the reflector, the anti-scatter grid having a plurality of plates, each plate extending along a length such that, when the CT detector is positioned in a CT system, the length of the plates extend approximately toward a focal spot of the CT system, the plurality of plates separated from one another at one of the first spacing and the second spacing, wherein two of the notches have a gap therebetween that engages one of the plates, and applying an adhesive to the gap to adhere the one plate to the reflector.

Disclosed also is a CT system that includes a rotatable gantry having an opening for receiving an object to be scanned, an x-ray tube having a focal spot from which x-rays emit, and a detector comprising one or more scintillator modules for receiving x-rays from the focal spot. Each of the scintillator modules includes a grid of pixelated scintillators extending in a first direction at a first spacing, and extending in a second direction, orthogonal to the first direction, at a second spacing, a reflector on the grid and between the pixelated scintillators, the reflector having a first thickness, the reflector forming a plurality of notches having a second thickness that is greater than the first thickness, and an anti-scatter grid having a plurality of plates, each plate extending along a length such that the length of the plates extend approximately toward the focal spot, the plurality of plates separated from one another at one of the first spacing and the second spacing, wherein two of the notches have a gap therebetween that engages one of the plates. An adhesive is positioned in the gap to adhere the one plate to the reflector. The system includes a computer programmed to acquire imaging data and generate an image.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A scintillator module for a CT detector, comprising:
   an array of pixelated scintillators extending in a first direction at a first spacing, and extending in a second direction, orthogonal to the first direction, at a second spacing;
   a reflector on the array and between the pixelated scintillators, the reflector having a first thickness, the reflector forming a plurality of notches having a second thickness that is greater than the first thickness;
   an anti-scatter grid having a plurality of plates, each plate extending along a length such that, when the CT detector is positioned in a CT system, the length of the plates extend approximately toward a focal spot of the CT system, the plurality of plates separated from one another at one of the first spacing and the second spacing, wherein two of the notches have a gap therebetween that engages one of the plates; and
   an adhesive positioned in the gap to adhere the one plate to the reflector.

2. The scintillator module of claim 1, wherein the first direction is a slice direction of the scintillator module and the second direction is a channel direction of the scintillator module.

3. The scintillator module of claim 1, wherein the anti-scatter grid is a two-dimensional (2D) collimator with the plurality of plates spaced from one another having the second spacing.

4. The scintillator module of claim 3, wherein the second spacing is in the channel direction of the scintillator module.

5. The scintillator module of claim 1, wherein the two notches are offset from one another in the first direction.

6. The scintillator module of claim 1, wherein the gap is approximately the same thickness as a thickness as one of the plates.

7. The scintillator module of claim 1, wherein each of the plurality of plates is positioned to cover a respective gap between the pixelated scintillators.

8. A method of fabricating a scintillator module for a CT detector, the method comprising:
   forming an array of pixelated scintillators extending in a first direction at a first spacing, and extending in a second direction, orthogonal to the first direction, at a second spacing;
   adhering a reflector to the array and between the pixelated scintillators, the reflector having a first thickness;
   forming a plurality of notches with the reflector, the notches having a second thickness that is greater than the first thickness;
   positioning an anti-scatter grid on the reflector, the anti-scatter grid having a plurality of plates, each plate extending along a length such that, when the CT detector is positioned in a CT system, the length of the plates extend approximately toward a focal spot of the CT system, the plurality of plates separated from one another at one of the first spacing and the second spacing, wherein two of the notches have a gap therebetween that engages one of the plates; and
   applying an adhesive to the gap to adhere the one plate to the reflector.

9. The method of claim 8, wherein the first direction is a slice direction of the scintillator module and the second direction is a channel direction of the scintillator module.

10. The method of claim 8, wherein positioning the anti-scatter grid comprises positioning a two-dimensional (2D) collimator with the plurality of plates spaced from one another having the second spacing.

11. The method of claim 10, wherein the second spacing is in the channel direction of the scintillator module.

12. The method of claim 8, wherein forming the plurality of notches comprises forming the two notches offset from one another in the first direction.

13. The method of claim 8, wherein the gap is approximately the same thickness as a thickness as the one plate.

14. The method of claim 8, further comprising positioning each of the plurality of plates to cover a respective gap between the pixelated scintillators.

15. A CT system comprising:
   a rotatable gantry having an opening for receiving an object to be scanned;
   an x-ray tube having a focal spot from which x-rays emit;
   a detector comprising one or more scintillator modules for receiving x-rays from the focal spot, each of the one or more scintillator modules comprising:
      an array of pixelated scintillators extending in a first direction at a first spacing, and extending in a second direction, orthogonal to the first direction, at a second spacing;
      a reflector on the array and between the pixelated scintillators, the reflector having a first thickness, the reflector forming a plurality of notches having a second thickness that is greater than the first thickness; and
      an anti-scatter grid having a plurality of plates, each plate extending along a length such that the length of the plates extend approximately toward the focal spot, the plurality of plates separated from one another at one of the first spacing and the second spacing, wherein two of the notches have a gap therebetween that engages one of the plates;
      an adhesive positioned in the gap to adhere the one plate to the reflector; and
   a computer programmed to acquire imaging data and generate an image.

16. The system of claim 15, wherein the first direction is a Z direction of the scintillator module and the second direction is a channel direction of the scintillator module.

17. The system of claim 15, wherein the anti-scatter grid is a two-dimensional (2D) collimator with the plurality of plates spaced from one another having the second spacing, and the second spacing is in the channel direction of the scintillator module.

18. The system of claim 15, wherein the two notches are offset from one another in the first direction.

19. The system of claim 15, wherein the gap is approximately the same thickness as a thickness as one of the plates.

20. The system of claim 15, wherein each of the plurality of plates is positioned to cover a respective gap between the pixelated scintillators.

* * * * *